United States Patent
Everhart et al.

(10) Patent No.: US 6,497,893 B1
(45) Date of Patent: Dec. 24, 2002

(54) SILK PROTEIN TREATMENT COMPOSITION AND TREATED SUBSTRATE FOR TRANSFER TO SKIN

(75) Inventors: Dennis Stein Everhart; Robert Cosmo Di Luccio, both of Alpharetta; Ali Yahiaoui, Roswell, all of GA (US); Wade Bolton May, Alexandria, LA (US); David John Tyrrell, Appleton, WI (US); Elizabeth Deibler Gadsby, Marietta, GA (US); Gunilla Elsa Gillberg-LaForce, Painted Post, NY (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/343,861

(22) Filed: Jun. 30, 1999

(51) Int. Cl.[7] .......................... A61N 25/34; A61F 13/06; A61K 51/00; A61K 7/09
(52) U.S. Cl. ...................... 424/402; 424/443; 424/1.69; 424/70.19; 424/70.21; 424/70.22; 514/865; 604/365; 604/367
(58) Field of Search .............................. 424/70, 56, 63, 424/443; 604/356, 357

(56) References Cited

U.S. PATENT DOCUMENTS

| 3,061,512 A | 10/1962 | Anderson, Jr. et al. | ........ 167/58 |
| 3,991,184 A | 11/1976 | Kludas et al. | .............. 424/177 |
| 4,233,212 A | 11/1980 | Otoi et al. | ................ 260/123.7 |

(List continued on next page.)

FOREIGN PATENT DOCUMENTS

| DE | 199 03 717 | 8/2000 |
| EP | 0 312 208 | 4/1989 |
| EP | 0 750 903 | 1/1997 |

(List continued on next page.)

OTHER PUBLICATIONS

Remington: The Science and Practice of Pharmacy. 19th ed. Gennaro AR, editor. Easton PA: Mack Publishing Co; 1995, chapter 67, pp. 1248–1267.

Manda, F. et al., "Skin lesions due to okra (*Hibiscus esculentus* L.): proteolytic activity and allergenicity of okra" *Contact Dermatitis* Feb.26, 1992(2):95–100.

Andersen, P.H. et al., "Faecal enzymes: in vivo human skin irritation" *Contact Dermatitis* Mar.30, 1994(3):152–158.

Buckingham, K.W. et al., "Etiologic factors in diaper dermatitis: the role of feces" *Pediatric Dermatology* Feb.3, 1986(2):107–112.

Franzke, C.W. et al., "Antileukoprotease inhibits stratum corneum chymotryptic enzyme. Evidence for a regulative function in desquamation" *J Bio Chem* Sep. 6, 1996;271(36):21886–90.

Katz, B.A. et al., "Design of potent selective zinc–mediated serine protease inhibitors." *Nature* Feb. 5:, 1998391(6667):608–12.

(List continued on next page.)

Primary Examiner—Thurman K. Page
Assistant Examiner—Isis Ghali
(74) Attorney, Agent, or Firm—William W. Letson; Lisa J. Moyles

(57) ABSTRACT

The present invention relates to a topical delivery system effective in depositing a thin, tenacious and substantially continuous coating of a silk protein on skin by an aqueous emulsion mediated dissolution of protein from a substrate with subsequent transfer and deposition onto the skin. Coatings of silk protein on skin resist removal, thereby providing a protective barrier against chemically- and biochemically-induced skin damage. The treatment composition also provides a vehicle for administering an effective dose of an active agent to the skin surface.

29 Claims, 7 Drawing Sheets

U.S. PATENT DOCUMENTS

| | | | |
|---|---|---|---|
| 4,344,967 A | 8/1982 | Easton et al. | 424/359 |
| 4,454,159 A | 6/1984 | Musher | 424/358 |
| 4,463,017 A | 7/1984 | Hidalgo et al. | 424/359 |
| 4,556,560 A | 12/1985 | Buckingham | 424/145 |
| 4,784,986 A | 11/1988 | Usher | 514/2 |
| 4,839,165 A * | 6/1989 | Hoppe et al. | 424/70 |
| 4,839,168 A * | 6/1989 | Abe et al. | 424/74 |
| 4,906,460 A | 3/1990 | Kim et al. | 424/70 |
| 4,973,473 A | 11/1990 | Schneider et al. | |
| 5,009,813 A | 4/1991 | Watanabe et al. | 252/545 |
| 5,069,898 A * | 12/1991 | Goldberg | 424/70 |
| 5,091,193 A * | 2/1992 | Enjolras et al. | 424/642 |
| 5,306,444 A | 4/1994 | Kitamura et al. | 252/546 |
| 5,385,696 A | 1/1995 | Repinec, Jr. et al. | 252/546 |
| 5,415,813 A * | 5/1995 | Misselyn et al. | 252/547 |
| 5,494,744 A * | 2/1996 | Everhatr et al. | 427/337 |
| 5,519,060 A | 5/1996 | Sprengeler et al. | 514/601 |
| 5,552,020 A | 9/1996 | Smith et al. | 162/164.4 |
| 5,604,200 A | 2/1997 | Taylor-McCord | |
| 5,609,587 A * | 3/1997 | Roe | 604/358 |
| 5,624,675 A | 4/1997 | Kelly | 424/405 |
| 5,637,616 A | 6/1997 | Sharpe et al. | 514/562 |
| 5,641,483 A | 6/1997 | Beaulieu | 424/78.06 |
| 5,648,389 A * | 7/1997 | Gans et al. | 514/557 |
| 5,676,967 A | 10/1997 | Williams et al. | |
| 5,693,515 A | 12/1997 | Clark et al. | 435/184 |
| 5,698,184 A | 12/1997 | Pickart | 424/59 |
| 5,728,461 A * | 3/1998 | Nogata et al. | 428/372 |
| 5,795,573 A | 8/1998 | Paradise | |
| 5,830,481 A | 11/1998 | Cauwet-Martin et al. | |

FOREIGN PATENT DOCUMENTS

| | | | | |
|---|---|---|---|---|
| EP | 0761867 A2 | 3/1997 | | |
| EP | 0763620 A2 | 3/1997 | | |
| EP | 0761867 A3 | 2/1998 | | |
| EP | WO 98/10134 | * | 3/1998 | D06M/15/03 |
| EP | 0841065 A2 | 5/1998 | | |
| EP | 0 842 605 | 5/1998 | | |
| EP | 0875233 | 11/1998 | | |
| EP | 0 875 233 | 11/1998 | | |
| GB | 2242198 | 9/1991 | | |
| JP | 11-50397 | 2/1999 | | |
| WO | 84/02845 | 8/1984 | | |
| WO | 91/02538 | 3/1991 | | |
| WO | 95/13806 | 5/1995 | | |
| WO | 96/03149 | 2/1996 | | |
| WO | 96/16681 | 6/1996 | | |
| WO | 98/10134 | 3/1998 | | |
| WO | 99/12504 | 3/1999 | | |
| WO | 99/12583 | 3/1999 | | |
| WO | 99/17738 | 4/1999 | | |
| WO | 99/32706 | 7/1999 | | |

OTHER PUBLICATIONS

Croda, Inc., Personal Care, CROSILKQUAT, "INCI Name: Cocodimonium Hydroxypropyl Silk Amino Acids", DS–14R–1, Jul. 6, 1994, p. 1–6.

Croda, Inc., Crodata: "CROSILK Liquid–Silk Amino Acids", p. 1–4

Croda, Inc., Crodata: "CROSILK Powder", p. 1–5.

Croda, Inc., Crodata: "CROSILK 10,000 (Hydrolyzed Silk)", p. 1–4.

Croda, Inc., Personal Care, CRODACOL Series, "INCI Names: CRODACOL C–70 Cetyl Alcohol; CRODACOL C–95 NF Cetyl Alcohol; CRODACOL S–70 Stearyl Alcohol; CRODACOL S–95 NF Stearyl Alcohol; CRODACOL CS–50 Cetearyl Alcohol; CRODACOL 1618 Cetearyl Alcohol", DS–81, May 31, 1995, p. 1–8.

Croda, Inc., Personal Care, CROSULTAINES (Vegetable Derived Hydroxysultaines), "INCI Names: CROSULTAINE C–50 Cocamidopropyl Hydroxysultaine; CROSULTAINE E–30 Erucamidopropyl Hydroxysultaine", DS–33R–1, Jun. 10, 1994, p. 1–9.

Centerchem, Inc., Certificate of Analysis, "Sericin", Jun. 21, 1996, 2 pages.

Croda, Inc., Croda Conservation International, Cronatural Brazil Nut Oil, "INCI Name: Brazil Nut (*Bertholletia Excelsa*) Oil", DS–68R–1, Apr. 22, 1994, p. 1–5.

English Translation of Abstract for JP 11–350,352 A.

English Abstract for DE 199 03 717 from corresponding WO 00/44343.

* cited by examiner

Sericin Treated Nonwoven
(a)Brightfield and (b)Fluorescent Image, both at 200x (a) (b)

SILK PROTEIN TREATMENT COMPOSITION AND TREATED SUBSTRATE FOR TRANSFER TO SKIN

FIELD OF THE INVENTION

This invention relates to the use of a treatment composition to enhance skin health. The treatment composition includes a surfactant and silk protein that can be applied to a substrate such as a nonwoven web, such that the composition will impart adequate fluid handling properties to the substrate and will subsequently be transferred to the skin for enhancing skin health. The treatment composition may further be used as a vehicle to deliver active agents to the skin.

BACKGROUND OF THE INVENTION

The skin is naturally an excellent barrier to the penetration of many foreign substances. From time-to-time, the natural ability of the skin to protect is compromised by external factors including abrasions, irritants and the like. Attempts have been made in recent years to promote skin health through the use of fiber products containing additives or developing synthetic or naturally occurring polymers that mimic or complement the properties of skin in order to maintain the skin health. An example of such a naturally occurring fiber includes silk fibers. Many attempts have been made to make skin-friendly materials from silk fibers. Manufacture of such fibers and materials therefrom, however, has been costly and difficult.

It is known that proteins naturally occurring in silk have enhancing properties when applied to skin and hair. Effective delivery of these silk proteins, as well as an active agent that can enhance or prevent damage to the underlying protective barrier of skin, is not yet known.

Enhancing skin health and delivering active agents to the skin to promote skin health has many advantages including: 1) protecting the skin and maintaining the skin in a moist state, essentially free from chapping or irritation, 2) pH buffering and barrier enhancement to maintain or enhance such base properties of skin, 3) inhibition of irritants that are suspected to promote irritant or allergic contact dermatitis, 4) maintaining the lubricity of skin, and 5) topical delivery of active agent compounds to improve utility of these compounds to improve the state of skin health.

The permeability of the skin to a foreign substance is influenced by a combination of physico-chemical parameters for both the object and the vehicle, if applicable, that delivers the object. Maintaining health of the skin and its underlying barrier properties requires optimal physico-chemical properties of the skin. The use of silk proteins such as sericin to improve these properties has never been completely optimized.

Sericin is one of two proteins that are part of the twin fibroin silk thread spun by Bombyx mori, a domestic insect. Sericin acts as a protective envelope around the fibroin thread as it is spun, which is like spinning of fibers with soluble sizing agents to help form good quality fibers. The sericin can be easily separated from silk protein by hydrolysis.

Post-spun sericin, with its unique properties, is known to have high affinity to a number of proteins. When refined to a high molecular weight substance it is amenable to binding to the keratin of skin and hair, forming a resistant, moisturizing, and protective film on the skin/hair, imparting good barrier properties.

Sericin is a silk protein obtained by controlled hydrolysis of low molecular weight silk having a specific gravity of at least about 1. A commercially available silk protein is available from Croda, Inc., of Parsippany, N.J., and is sold under the trade name CROSILK LIQUID (silk amino acids), CROSILK 10,000 (hydrolyzed silk), CROSILK POWDER (powdered silk), and CROSILKQUAT (cocodimonium hydroxypropyl silk amino acid). Another example of a commercially available silk protein is SERICIN, available from Pentapharm, LTD, a division of Kordia, bv, of the Netherlands. Further details of such silk protein mixtures can be found in U.S. Pat. No. 4,906,460, to Kim, et al., assigned to Sorenco, which is herein incorporated by reference in its entirety.

Sericin can be adapted for topical delivery by a compound that is specifically designed to provide a therapeutic effect only to the local area to which the compound is applied. Furthermore, topical formulations are often designed to prevent any systemic delivery of the compound in order to localize its use. Depending on the vehicle, topical delivery of a compound can result in predictable and reliable delivery of an agent to promote skin health.

U.S. Pat. No. 5,728,461 to Nogata et al., assigned to Seiren, Co., Ltd., discloses a protein (e.g. sericin) applied to a surface of a fiber whereby the fiber forms a textile fabric such as a tight or pantyhose. When the pantyhose was in contact with human skin, the sericin was mechanically applied/transferred to the skin to maintain the skin in a moist state, thereby preventing chapping and senescence of the skin.

European Patent Application No. 0,841,065 A2 to Yamada, et al., published May 13, 1998, discloses topically applied compositions that are useful as an antioxidant or as an inhibitor for tyrosinase activity, in order to prevent skin pigmentation or blotches caused by melanin formation.

U.S. Pat. No. 5,415,813 to Misselyn, et al., assigned to Colgate-Palmolive Company discloses the use of 0.01 to 3% of a silk protein as a skin friendly ingredient in an all-purpose liquid cleaning emulsion composition.

There is a need for a treatment composition for use with a substrate that is capable of delivering a thin, tenacious, substantially continuous film of the silk protein to the skin that can prevent or reduce skin irritation, maintain pH, maintain skin hydration, lubrication, and aid as a vehicle for the topical delivery of active agent compounds. The composition of the instant invention fulfills this need. Additionally, while skin wellness additives are known, other compositions have had the undesired side effect of reducing wettability, or the fluid intake rate, of the substrate. There remains a need for a treatment composition for application and use with a substrate that will not adversely affect fluid properties of the substrate, e.g. fast and sustainable fluid intake rate.

SUMMARY OF THE INVENTION

The present invention relates to a composition for surface treatment of a substrate, e.g. a nonwoven web, used in personal care product applications. The surface treatment combination not only provides adequate fluid handling properties, but also provides a topical delivery system effective in depositing a thin, tenacious and substantially continuous coating of a silk protein on skin by an aqueous emulsion mediated dissolution of protein from a substrate with subsequent transfer and deposition onto the skin. Coatings of silk protein on skin resist removal, thereby providing a protective barrier against chemically- and biochemically-induced skin damage. The treatment composition also provides a vehicle for administering an effective dose of an active agent to the skin surface. Also provided is a treatment composition for application and use with a substrate that will not adversely affect fluid properties of the substrate, e.g. fast and sustainable fluid intake rate as long as the material/product is being used.

DETAILED DESCRIPTION OF THE INVENTION

Figure 1:
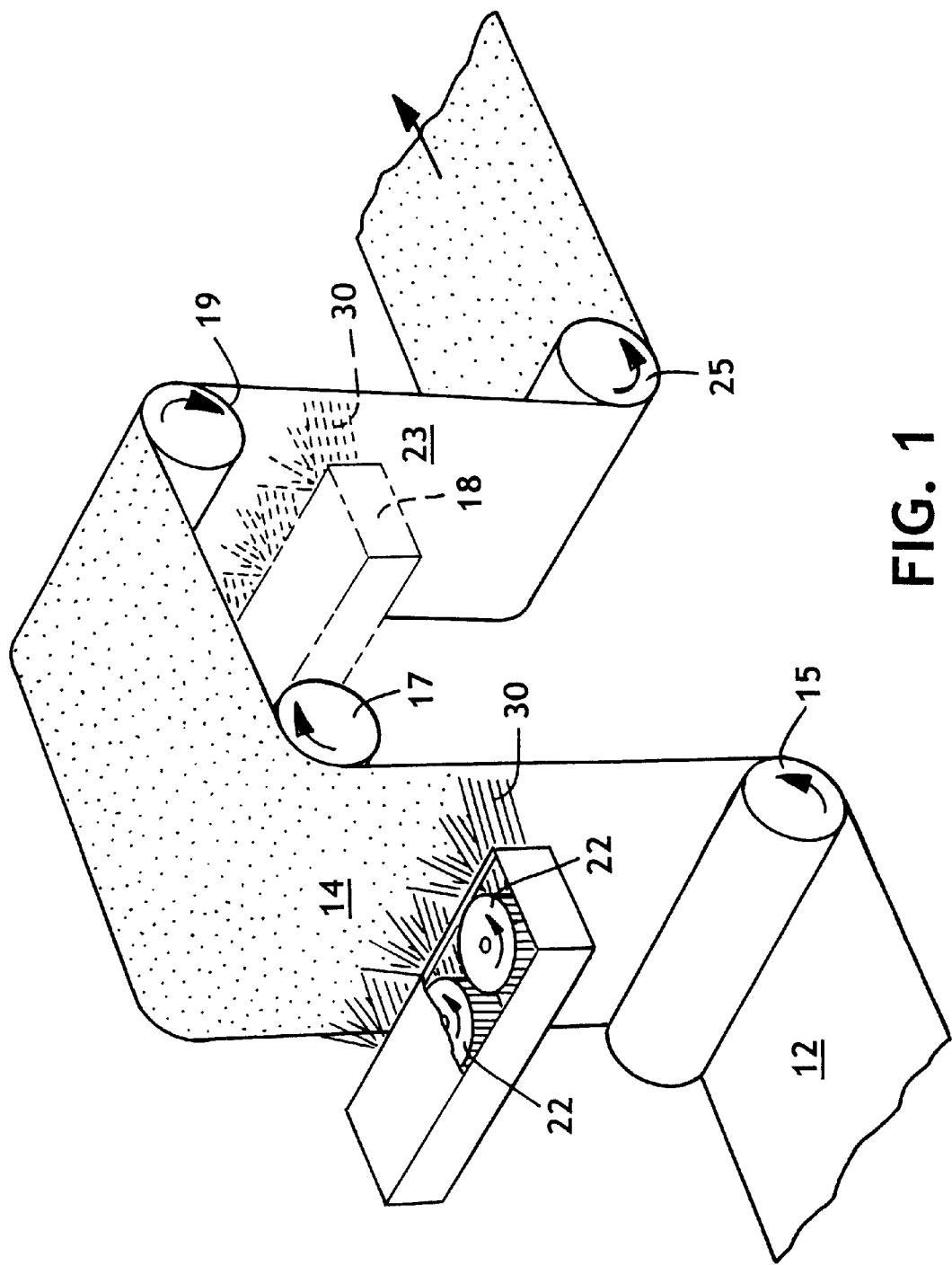
FIG. 1 is a schematic illustration of a treating process useful for application of the treatment composition of the present invention to one or both sides of the nonwoven web.

Compositions and methods are provided by the present invention for topical administration of skin treatment compositions to the skin of mammals, especially humans, to protect the skin by preserving and restoring the natural integrity of the skin. This is achieved by depositing a protective protein from a substrate that is able to control the release of the protein to the surface of the skin. The protein acts as a protectorant that is capable of maintaining the pH of the skin, inhibit the activity of irritants to the skin, maintain skin hydration, and lubrication. Pancreatic digestive enzymes that are expelled by the body with feces have been implicated to induce skin inflammation (Anderson, P. H., Bucher, A. P., Saees, Ill., Lee, P. C., Davis, J. A., and Maibach, H. I., *Faecal enzymes: in vivo skin irritation.* Contact Dermatitis 1994; 30, 152–158). When the feces, including these enzymes, contact the skin, the skin becomes irritated. In some cases, proteases, e.g. fecal and urine proteases, cleave stratocorneum proteins, thereby breaking down the natural protective barrier of the skin, and leaving the skin susceptible to irritation by enzymes. The treatment composition of the present invention is designed to form a thin, tenacious, substantially continuous film over the skin to inhibit, or at least minimize, the effect of such fecal irritants.

The treatment composition of the present invention includes a surfactant and a silk protein. Preferably, the treatment composition is prepared as an emulsion of the surfactant and silk protein, usually as an oil-in-water (o/w) emulsion.

Examples of emulsions include aqueous emulsions of commercially available silk proteins, e.g. SERICIN and CROSILK, and surfactants, e.g. AHCOVEL Base N-62 (hereinafter "AHCOVEL"), a mixture of sorbitan monooleate and polyethoxylated hydrogenated castor oil, manufactured by Hodgson Co. It has been found that when emulsions containing about 75 wt. % surfactant and up to about 25 wt. % silk protein at about 0.1 to 40 wt. % total solids are used, sufficient amounts of silk protein and other ingredients transfer to the skin. Preferably, the emulsions will contain between about 5 to 30 wt. % solids. These emulsions can either be applied onto a substrate from a high-solids bath (up to 40 wt. %) or from dilute baths ranging from 0.1 wt. % to about 20 wt. %. Preferably, the emulsion will be diluted to about 0.5 wt. % to about 15 wt. %.

The concentration of the silk proteins in these formulations can vary widely, and will be selected primarily by intended use, viscosity, etc., in accordance with the particular indication and mode of administration selected. Actual methods of preparing such dosage forms are known, or will be apparent, to those skilled in this art; for example, see Remington's Pharmaceutical Science, Mack Publishing Company, Easton, Pa., 19th ed., 1995, which is incorporated herein by reference. The composition or formulation to be transferred to the skin, in any event, contain a quantity of the silk protein sufficient to achieve the desired therapeutic or prophylactic effect.

The silk protein derivatives may be chosen from one of several potential compositions. Included among the silk derivatives are silk fibers and hydrolysate of silk fibers. The silk fibers may be used in the form of powder in preparing the emulsion or as a powder of a product obtained by washing and treating the silk fibers with an acid. Preferably, silk fibers are used as a product obtained by hydrolysis with an acid, alkali or enzyme, as disclosed in U.S. Pat. No. 4,839,168 to Abe et al.; U.S. Pat. No. 5,009,813 to Watanube et al., and U.S. Pat. No. 5,069,898 to Goldberg, each incorporated herein by reference in its entirety.

Another silk derivative that may be employed in the composition of the present invention is protein obtained from degumming raw silk, as disclosed, for example, in U.S. Pat. No. 4,839,165 to Hoppe et al., incorporated herein by reference in its entirety. The principal protein obtained from the raw silk is sericin, which has an empirical formula of $C_{15}H_{25}O_3N_5$ and a molecular weight of about 323.5.

A preferred silk derivative is a mixture of two or more individual amino acids, which naturally occur in silk. The principal silk amino acids are glycine, alanine, serine and tyrosine.

Another example of a silk derivative for use in the emulsion composition of the present invention is a fine powder of silk fibroin in nonfibrous or particulate form, as disclosed in U.S. Pat. No. 4,233,212 to Otoi et al., incorporated herein by reference in its entirety.

The fine powder is produced by dissolving a degummed silk material in at least one solvent selected from, for example, an aqueous cupriethylene diamine solution, an aqueous ammonia solution of cupric hydroxide, an aqueous alkaline solution of cupric hydroxide and glycerol, an aqueous lithium bromide solution, an aqueous solution of the chloride, nitrate or thiocyanate of calcium, magnesium or zinc and an aqueous sodium thiocyanate solution. The resulting fibroin solution is then dialyzed. The dialyzed aqueous silk fibroin solution, having a silk fibroin concentration of from about 3 to 20% by weight, is subjected to at least one treatment for coagulating and precipitating the silk fibroin, such as, for example, by the addition of a coagulating salt, by aeration, by coagulation at the isoelectric point, by exposure to ultrasonic waves, by agitation at high shear rate and the like.

The resulting product is a silk fibroin gel, which may be incorporated directly into a treatment composition or the same may be dehydrated and dried into a powder and then dissolved in the treatment composition.

The silk material used to form the silk fibroin includes cocoons, raw silk, waste cocoons, raw silk waste, silk fabric waste and the like. The silk material is degummed or freed from sericin by a conventional procedure such as, for example, by washing in warm water containing a surfactant-active agent or an enzyme, and then dried. The degummed material is dissolved in the solvent and preheated to a temperature of from about 60 to 95° C., preferably of from about 70 to 85° C. Further details of the process of obtaining the silk fibroin are discussed in previously referenced U.S. Pat. No. 4,233,212.

Turning again to the surfactants useful in the treatment composition of the present invention, the surfactant will provide superior fluid handling performance, skin protection and mildness to human skin. Useful examples of the surfactant include ethoxylated hydrogenated fatty oils, monosaccharides, monosaccharides derivatives, polysaccharides, polysaccharide derivatives, and combinations thereof.

Water miscible nonionic surfactants are preferred and such surfactants are commercially available. Examples of such surfactants include AHCOVEL and Glucopon 220UP, available from Henkel Corporation, which is an alkylpolyglycoside having 8 to 10 carbons in the alkyl chain, and may also be used as a part of the surfactant. Other well known nonionic surfactants are the primary aliphatic alcohol ethoxylates, secondary aliphatic alcohol ethoxylates, alkylphenol ethoxylates and ethylene-oxide-propylene oxide condensates on primary alkanols, such as PLURAFACS and PLURONICS (available from BASF, Inc.) and condensates of ethylene oxide with sorbitan fatty acid esters such as TWEEN (also available from Uniqema). The nonionic surfactants generally are the condensation products of an organic aliphatic or alkyl aromatic hydrophobic compound and hydrophilic ethylene oxide group. Practically any hydrophobic compound having a carboxy, hydroxy, amido, or amino group with a free hydrogen attached to the nitrogen can be condensed with ethylene oxide or with the polyhydration product thereof, polyethylene glycol, to form a water miscible nonionic surfactant. Other suitable surfactants include polyoxyethylene sorbitan monolaurate, polyoxyethylene sorbitan monostearate, polyoxyethylene sorbitan trioleate, polyoxyethylene sorbitan tristearate, and bovine lipid extract surfactant (Survanta, Ross Laboratories), a drug used to treat Acute Respiratory Distress Syndrome and Cystic Fibrosis, and enzymes such as papain or pepsin which cleave protein structures.

More specifically, the nonionic surfactant may include the condensation products of a higher alcohol (e.g., an alkanol containing about 8, 9, 10, 11, 12, 13, 14, 15, 16, 17 or 18 carbon atoms in a straight or branched chain configuration) condensed with about 5 to 30 moles of ethylene oxide. Examples include: lauryl or myristyl alcohol condensed with about 16 moles of ethylene oxide (EO); tridecanol condensed with about 6 moles of EO; myristyl alcohol condensed with about 10 moles of EO per mole of myristyl alcohol; the condensation product of EO with a cut of coconut fatty alcohol containing a mixture of fatty alcohols with alkyl chains varying from 10, 11, 12, 13 or 14 carbon atoms in length and wherein the condensate contains either about 6 moles of EO per mole of total alcohol or about 9 moles of EO per mole of alcohol; and tallow alcohol ethoxylates containing 6 EO to 11 EO per mole of alcohol. Condensates of 2 to 30 moles of ethylene oxide with sorbitan mono- and $3C_{10}$–$C_{20}$ alkanoic acid esters having a HLB (hydrophilic/lipophilic balance) of about 4 to 20, preferably about 8 to 15, may also be employed as the nonionic surfactant.

Another class of surfactant compounds include the alkyl polysaccharides. Alkyl polysaccharides are alkyl polyglycosides having the formula SUGAR-O-R, where R is a hydrophobic group.

Compositions and methods are also provided by the present invention for topical administration of the protein concurrently with a biologically active agent that can be administered topically in a controlled manner. Examples of such substances include active agents such as multivalent metal compounds including zinc salt, zinc sulfate monohydrate, and the like. These active agents are particularly useful as astringents and enzyme inhibitors. The amount of active agent will be introduced in the composition described above in the range of from about 0.01% to about 10% by weight of the composition. Preferably, the active agent will be present in the amount of about 0.25% to about 1% by weight of the composition.

In addition to the silk protein of the treatment composition of the present invention, an additional protein may be present in the amount of about 0.1 to about 4.0% by weight. This additional protein may be selected from the group consisting of hydrolyzed animal collagen protein obtained by an enzymatic hydrolysis, lexeine protein, vegetal protein and hydrolyzed wheat protein and mixtures thereof.

The composition of the present invention can be in the form of an oil-in-water (o/w) emulsion or after dilution with water, with the essential ingredients being water, surfactant, and/or co-surfactant.

Because the composition as prepared is an aqueous liquid formulation and since no particular mixing is required to form the o/w emulsion, the composition is easily prepared simply by combining all the ingredients in a suitable vessel or container. The order of mixing the ingredients is not particularly important and generally the various ingredients can be added sequentially or all at once or in the form of aqueous emulsions of each or all of the primary surfactants and co-surfactants can be separately prepared and combined with each other. It is important to note that emulsions of, for instance, organic acid emulsions would not be acceptable for use in the present invention, since such emulsions would be a strong skin irritant and counterproductive to the intended use of the present invention. The active agent, when present, can be added as an aqueous emulsion thereof or can be added directly. It is not necessary to use elevated temperatures in the formation step and room temperature is sufficient. However, higher temperatures of up to about 180° F. (82.2° C.), preferably 110 to 140° F. (43.3 to 60° C.), can also be used.

For administration to the skin of a human or other mammal, the treatment compositions will often be sterilized or formulated to contain one or more preservatives for incorporation into pharmaceutical, cosmetic or veterinary formulations. These treatment compositions can be sterilized by conventional, well-known sterilization techniques, e.g., boiling or pasteurization, without substantially adversely affecting the biological activity of the composition. The compositions may contain pharmaceutically acceptable auxiliary substances as required to approximate physiological conditions and as necessary to prepare compositions for convenient administration, such as pH adjusting and buffering agents, preservatives, and delivery vehicles. Actual methods for preparing pharmaceutically administrable compounds will be known or apparent to those skilled in the art and are described in detail in, for example, Remington's Pharmaceutical Science, supra.

Perfumes, dyes and pigments can also be incorporated into the treatment compositions of the invention. For semisolid compositions, as would be appropriate for pastes and creams intended for topical administration, the peptone-copper complexes can be provided separately or may be compounded with conventional nontoxic carriers such as, for example, aloe vera gel, squalene, glycerol stearate, polyethylene glycol, cetyl alcohol, stearic acid, and propylene glycol, among others. Such compositions may contain about 5–100% active ingredients, more preferably about 5–25%.

The compositions formulated for administration to the skin are administered to a wearer, such as humans, with un-compromised skin or in situations where a subject is already suffering from damaged skin (e.g., peeling) due to ultraviolet or other irradiation or oxidative skin damage. The treatment compositions are administered in an amount sufficient to allow inhibition of further damage by topically administered irritating substances or other unknown irritating substances and are more effective than if the host were not treated. Amounts adequate to accomplish these effects are defined as a "therapeutically effective dose" and will vary according to the application.

In prophylactic and cosmetic applications the compositions are employed for protecting the skin from damage. Thus, the silk proteins or silk proteins and active agents are administered to a host under conditions which protect the integrity of the skin, maintains physiological pH, skin hydration and lubrication. In these uses the precise amounts again depend on the amount of protection desired and the extent and conditions under which the skin is exposed to potentially damaging conditions, such as those caused by fecal proteases, urine, or other irritating substances. They can generally range from about 0.1 mg to about 10 mg per day per square centimeter of skin. Single or multiple administrations of the compositions can be carried out daily or over a prolonged period of time.

The silk proteins of the invention may be administered to the skin in relatively large amounts without serious side effects, although indiscriminate use may produce irritation of the skin. In instances where the compositions are administered prophylactically to inhibit oxidative or biochemical damage to the skin or to those suffering from only mild skin damage, irritation or inflammation of the skin, the dose may be adjusted to lower maintenance levels.

The treatment composition providing skin protection and enhanced repair of the present invention, including pharmaceutical compositions, may be administered alone or as combination or adjunct therapy or prophylaxis. For example, the treatment compositions can be used in combination with other skin protective factors or those found to improve other aspects of protection or healing. In this manner a synergistic effect may be attained that yields a clinical efficacy greater than that realized with any single factor.

Further, while the compositions described herein stimulate a spectrum of skin protective processes, skin can differ considerably in its properties, leading one to utilize a combination of a composition described herein and another compound or factor.

Factors with reported healing properties which can be included with the silk protein compositions for use in protective/healing formulations and methods of the present invention include, for example, epidermal growth factor, fibroblast growth factor, nerve growth factor, transforming growth factors, angiogenic growth factors, heparin, fibronectin, fibrin, platelet-derived growth factor, enzymatic superoxide dismutase, extracts of blood or factors from the blood, and other similar factors.

Substrates particularly adapted to receive exudate liquids such as menses, mucous, blood products, feces, and others, which will be apparent to those skilled in the art, are useful in the present invention. As used herein, the term "substrate" refers to a material that can be a woven fabric, knit fabric, nonwoven fabric, foam, film-like material (e.g. an apertured film-like material) or paper material. Particularly useful substrates include infant and child care products such as disposable diapers, training pants and baby wipes, feminine hygiene products such as menses absorbing devices like sanitary napkins and tampons, bandages, and incontinent products, for example. In accordance with the invention the substrate is often normally hydrophobic and contains a treatment composition placed so as to contact the exudate. Many polymers useful in the formation of nonwoven webs, e.g. polypropylene, are hydrophobic and highly apolar. As is known to those skilled in the art, sericin is highly hydrophilic, hence it is polar. There is, therefore, no affinity between the substrate and the silk protein, making it difficult to apply the silk protein to the substrate. The unique combination of the silk protein with the surfactants of the present invention overcomes this lack of affinity. In other words, the surfactant serves as a medium to carry the silk protein for application to the substrate. As would be understood by those skilled in the art, some synthetic fibers, such as nylon, are hydrophilic, and would not therefore have this particular problem addressed with the present invention.

Advantageously the substrate is a nonwoven web and may be, for example, a spunbond, meltblown, coformed or bonded carded web. Additional substrates which can be used include foams and films that are fibrillated, apertured or otherwise treated to have fiber-like properties as well as laminates of these and/or nonwoven webs. Depending on the particular application, the substrate may be used as a body contact liner, a distribution layer between a liner and an absorbent layer, an absorbent layer, or in more than one of these layers.

As used herein the term "nonwoven fabric or web" means a web having a structure of individual fibers or threads, which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, coforming processes and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 50 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface and usually subjected to a separate bonding step. Spunbond fibers are generally continuous and have average diameters frequently larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly dispersed meltblown fibers. Such a process is disclosed, for example, in U.S. Pat. No. 3,849,241 to Butin. Meltblown fibers are microfibers which are usually continuous, but which may also be discontinuous, and are generally smaller than 10 microns in average diameter.

The substrate of the present invention may also include a bonded carded web. As used herein "bonded carded webs" or "BCW" refers to nonwoven webs formed by carding processes as are known to those skilled in the art and further described, for example, in coassigned U.S. Pat. No. 4,488,928 to Alikhan and Schmidt which is incorporated herein by reference in its entirety. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven material.

As would be understood by one of ordinary skill in the art, such nonwoven webs may be formed from different types of polymers, which may be extruded as monocomponent fibers, biconstituent fibers and/or conjugate fibers (multi- and bicomponent fibers) filaments. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277. Conjugate fibers are taught in U.S. Pat. No. 5,108,820 to Kaneko et al., U.S. Pat. No. 5,336,552 to Strack et al., and U.S. Pat. No. 5,382,400 to Pike et al.

Small amounts of additives may be added for color, anti-static properties, lubrication, hydrophilicity, antibacterial, antimold, deodorizing effect, and the like. These additives, e.g. titanium dioxide for color and chitosan as an antibacterial, are generally present in an amount less than 5 weight percent and more typically about 2 weight percent.

As used herein, the term "personal care product" includes diapers, training pants, swim pants, absorbent underpants, adult incontinence products, sanitary wipes, feminine hygiene products such as sanitary napkins and tampons, wound dressings and bandages.

As used herein, the term "hydrophilic" means that the polymeric material has a surface free energy such that the polymeric material is wettable by an aqueous medium, i.e. a liquid medium of which water is a major component. The term "hydrophobic" includes those materials that are not hydrophilic as defined. Hydrophobic materials may be treated internally or externally with surfactants and the like to render them hydrophilic.

The substrate of the present invention may be a multilayer laminate. An example of a multilayer laminate is an embodiment wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al, and U.S. Pat. No. 4,374,888 to Bornslaeger. Such substrates usually have a basis weight of from about 0.1 to 12 osy (6 to 400 gsm), or more particularly from about 0.75 to about 3 osy.

Spunbond nonwoven fabrics are generally bonded in some manner as they are produced in order to give them sufficient structural integrity to withstand the rigors of further processing into a finished product. Bonding can be accomplished in a number of ways such as hydroentanglement, needling, ultrasonic bonding, adhesive bonding, stitchbonding, through-air bonding and thermal bonding such as calendering.

The addition of the treatment composition to the substrate may be accomplished by conventional means such as spraying, coating, dipping and the like although the use of high solids spray is advantageous in cases where drying and/or compression is desired to be minimized. The amount of the treatment composition used will depend on the particular end use as well as factors such as basis weight and porosity of the substrate. Referring to FIG. 1, an exemplary process will be described for application to one or both sides of a traveling substrate. It will be appreciated by those skilled in the art that the invention is equally applicable to inline treatment or a separate, offline treatment step. Substrate 12, for example a spunbond or meltblown nonwoven web is directed over support rolls 15,17 to a treating station including rotary spray heads 22 for application to one side 14 of web 12. An optional treating station (shown in phantom) which may include rotary spray heads 18 can also be used to apply to opposite side 23 of substrate 12. Each treatment station receives a supply of treatment composition 30 from a reservoir (not shown). The treated substrate may then be dried if needed by passing over dryer cans 25 or other drying means and then wound as a roll or converted to the use for which it is intended. Alternative drying means include ovens, through air dryers, infra red dryers, air blowers, and the like.

As referred to above, a unique and surprising aspect of the present invention includes the ability of the treatment composition to be transferred from the substrate to the skin. It has been found that when a liquid is introduced to the substrate, the treatment composition will dissolve in the liquid, and then liquid-mediated transfer of the treatment composition to the skin occurs. In other words, the treatment composition including the silk protein dissolves off of the substrate into the liquid, which then deposits the thin, tenacious and substantially continuous film of silk protein onto the skin. Urine is an example of a liquid that can transfer the treatment composition from the substrate to the skin. As another example, the liquid generated by the body after abrasion or injury to the skin, might provide sufficient liquid-mediated transfer of the treatment composition from the substrate, in this case, a bandage or wound dressing. In general, when wetness increases, the treatment composition will transfer to the skin to form a protective barrier.

Figure 2:
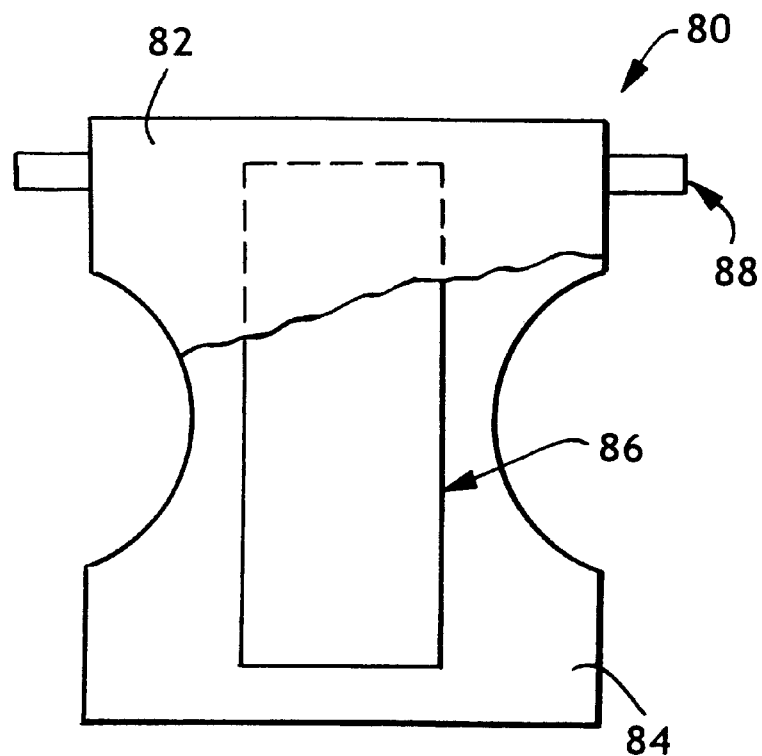
FIG. 2 is a partially cut-away top plan view of an exemplary personal care product, in this case a diaper, which may utilize the treated substrate according to the present invention.

An exemplary article 80, in this case a diaper, is shown in FIG. 2. Referring to FIG. 2, most such personal care absorbent articles 80 include a liquid permeable top sheet or liner 82, a barrier back sheet or outercover 84 and an absorbent core 86 disposed between and contained by the top sheet 82 and back sheet 84. Articles 80, such as diapers, may also include some type of fastening means 88 such as adhesive fastening tapes or mechanical hook and loop type fasteners to maintain the garment in place on the wearer. The substrate 12 may be used to form various portions of the article including, but not limited to the top sheet or liner 82.

The following examples are offered by way of illustration, not by way of limitation.

EXAMPLES

The compositions of the present invention were formed by creating an emulsion (or microemulsion) of a silk protein and water as the carrier liquid. Aqueous emulsions of SERICIN and CROSILK as the silk protein, AHCOVEL, as the surfactant system, and zinc salt as the active agent, were prepared. The stable emulsions were diluted to about a 5% by weight emulsion and applied to the surface of a polyolefin nonwoven liner fabric at 3 and 6% by weight via a saturation dip and squeeze process as described in more detail below. The fabrics were then tested for fluid intake rate, softness, skin transfer, skin barrier, anti-inflammatory, and the like, as describe in more detail below.

Fluid Intake Rate: This test is identified as Fluid Strikethrough EDANA 150.1-90 and measures the time taken for a known volume of liquid (simulated urine) applied to the surface of a nonwoven test sample in contact with an underlying absorbent pad to pass through the nonwoven. In general, a 50 ml burette is positioned on a ring stand with the tip inside a funnel. A standard absorbent pad of 5 plies of specified filter paper (482% absorbency) is placed on an acrylic glass base plate below the funnel, and a nonwoven sample is placed on top of the absorbent. An acrylic glass strike-through plate 25 mm thick and weighing 500 g is placed over the sample with the cavity centered 5 mm below the funnel. The burette is filled with liquid, keeping the funnel closed, and a quantity of the liquid (e.g., 5 ml or 10 ml) is run into the funnel. The 5 ml or 10 ml is allowed to discharge starting a timer which stops when the liquid has penetrated into the pad and fallen below a set of electrodes, and the elapsed time is recorded. The liquid used was Blood Bank Saline, available from Stephens Scientific Co., Catalog No. 8504.

Softness Test: Although a specific softness test was not conducted, each of the samples prepared were noted to have a "soft hand", and would be suitable for use in articles as described herein.

Skin Transfer Test: Sericin was labeled with the fluorescent dye, Texas Red (TR), according to the procedure suggested by Molecular Probes, Inc., Eugene Oreg. (Texas Red protein labeling kit F-6162). A 4.5 wt. % solution of sericin, 200 uL, was reacted with 100 uL of a 5 mg/mL solution of Texas Red succinimide in dimethylsulfoxide for 1 hour. The thus labeled protein was isolated via gel chromatography with centrifugation for 3 minutes at 1100×g.

Figure 3:
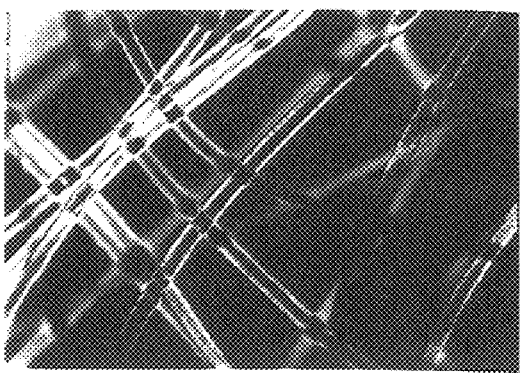
FIG. 3 is a 200× optical microscopy (Brightfield and Fluorescent Image) of a substrate treated with the treatment composition according to the present invention.
Figure 3:
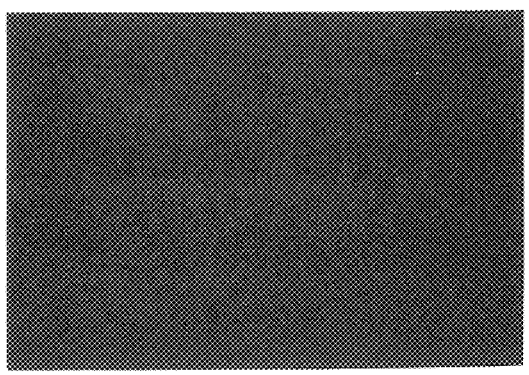

Solutions of Ahcovel containing a mixture of TR labeled and unlabelled sericin was used to treat a substrate of 0.6 osy polypropylene spunbond nonwoven web, prepared as a diaper liner according to the procedure described. Fluorescent microscopy using a high pressure Hg lamp with excitation and emission bandpass filters of 595 nM and 615 nM, respectively, confirmed the presence of the labeled protein on the substrate. FIG. 3 is a 200× optical microscopy (Brightfield and Fluorescent Image) of the substrate treated with the treatment composition according to the present invention. The untreated substrate showed no significant fluorescence, (not shown).

Figure 4:
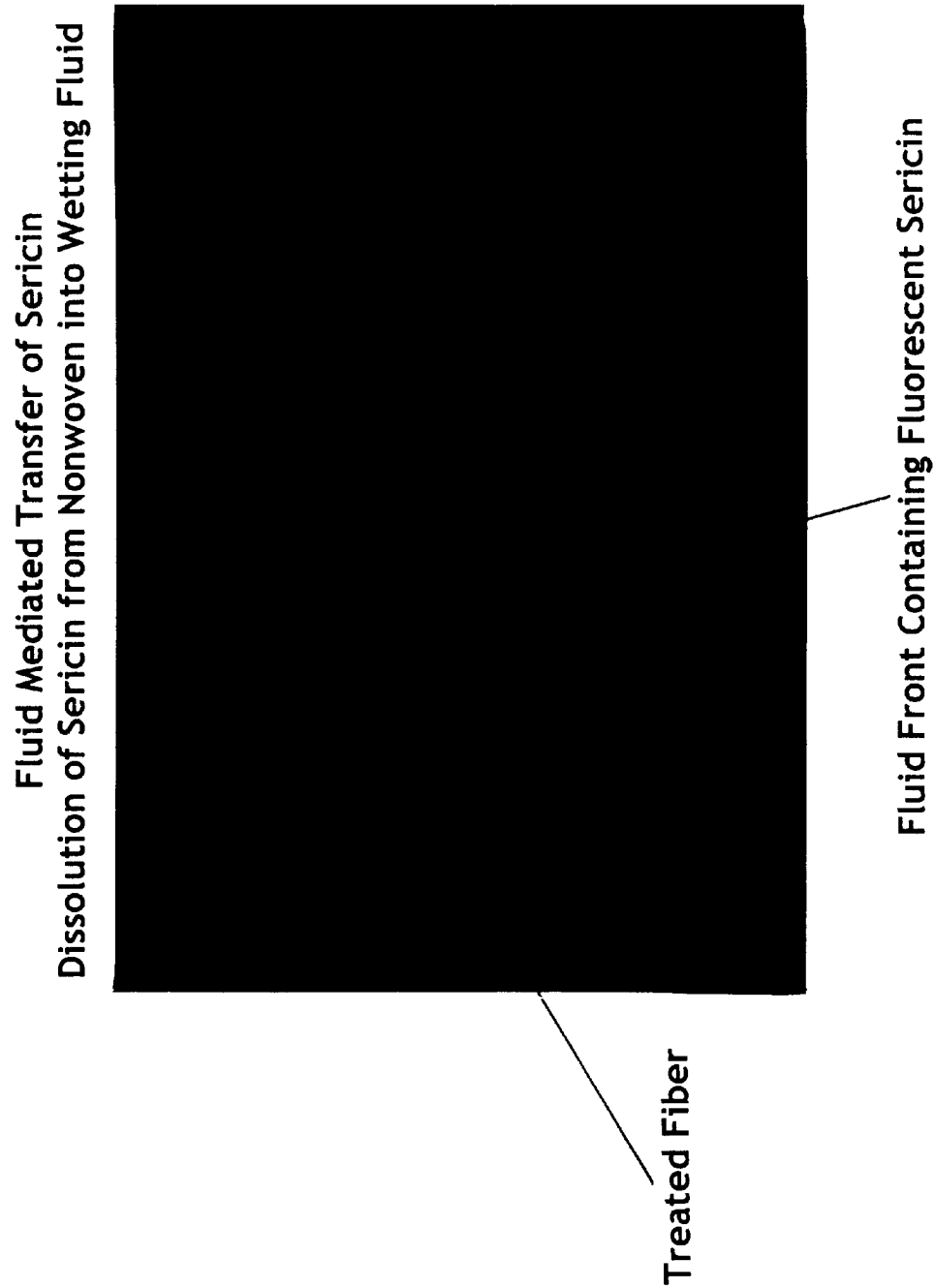
FIG. 4 is a 200× optical microscopy (Fluorescent Image) showing the liquid mediated transfer of the treatment composition from the treated substrate and dissolving in the liquid.

Upon exposing the treated substrate to water, intense fluorescence, characteristic of TR, could be detected in solution, suggesting solubility of the labeled protein into the wetting media. Sericin was removed from the substrate due to its solubility in water. FIG. 4 is a 200× optical microscopy (Fluorescent Image) showing this liquid mediated transfer of the treatment composition from the treated substrate and dissolving in the liquid.

Figure 5:
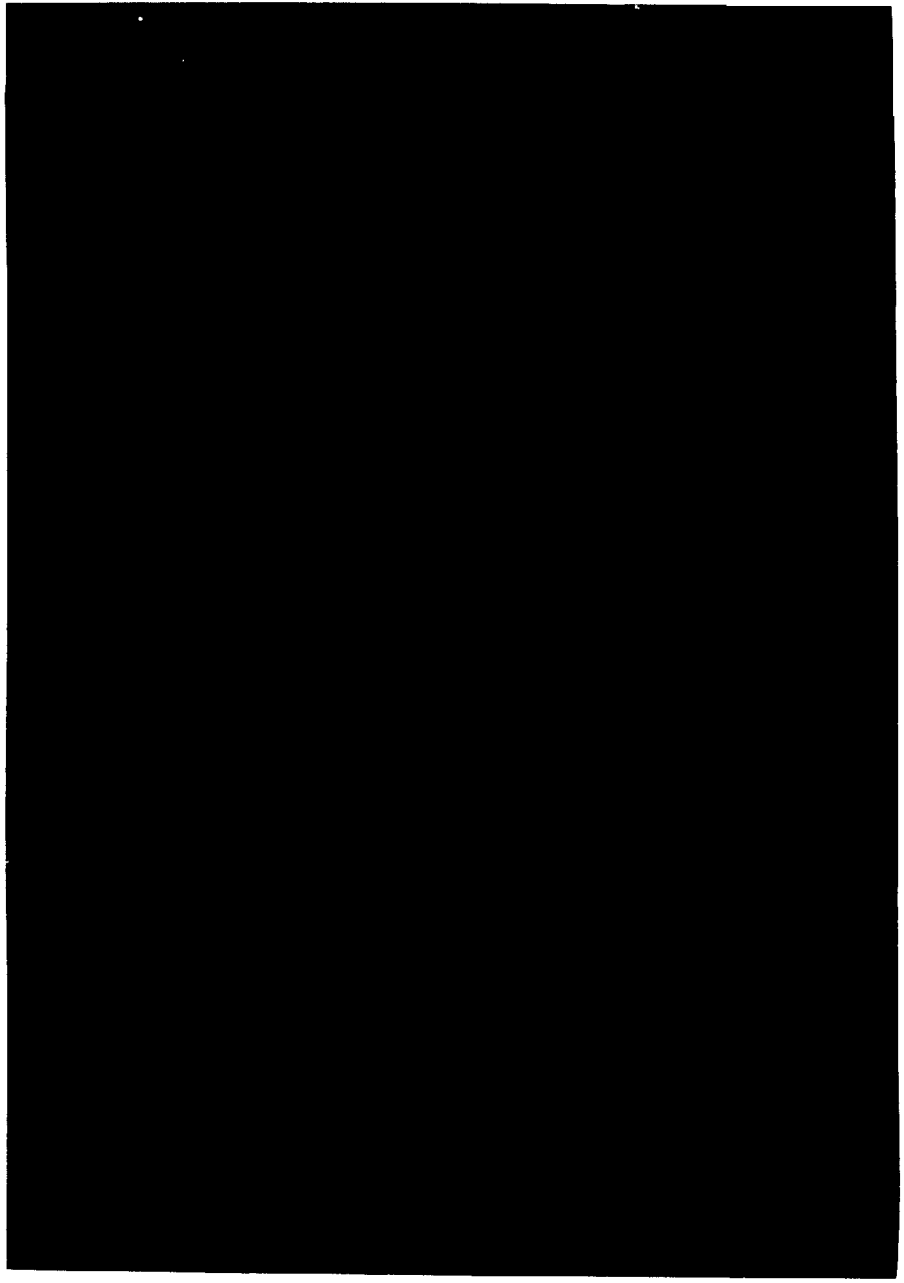
FIG. 5 is a 200× optical microscopy (Fluorescent Image) of skin that has been treated with the treatment composition including liquid mediated transfer of the composition to the skin, wherein the silk protein has been labeled with a fluorescent dye to show the transfer of a thin, tenacious, substantially continuous film to the skin.
Figure 6:
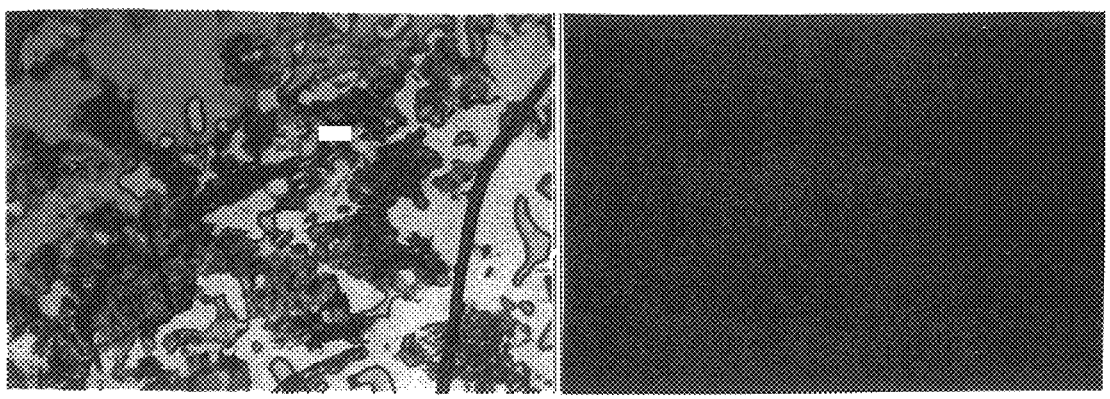
FIG. 6 is a 100× optical microscopy (Brightfield and Fluorescent Image) of skin that has been treated in accordance with the prior art in that the treatment composition has been transferred to the skin by mechanical transfer, wherein the silk protein has been labeled with a fluorescent dye to show the transfer of a substantially discontinuous film to the skin.

Transfer of the labeled protein from the treated substrate to the skin was verified by the following procedure. A 1 $cm^2$ square of treated substrate was secured to the volar forearm with adhesive tape. A majority of the area of the substrate was not covered with tape, which was placed only on the perimeter to secure the substrate to the arm. The substrate was subsequently wetted with 300 uL of water. After several minutes, the substrate was removed from the arm, and the stratum corneum previously covered by the material was tape stripped with Dsquame tape to remove superficial layers of skin for fluorescent microscopic analysis. Microscopy at 100× and 200× clearly revealed intense fluorescence associated with the TR labeled protein, thus confirming that transfer from the substrate to the skin, mediated by wetting, was conclusive. FIG. 5 shows the thin, tenacious, substantially continuous film of silk protein that was applied to the skin by means of the present invention. The morphology of the resulting protein coating was consistent with a thin, tenacious, substantially continuous film of the sericin protein on the corneocytes of the forearm. FIG. 6, on the other hand, shows the variability of application of the silk protein by means of mechanical transfer described in the prior art.

The fabrics were then tested for topical delivery of the zinc salt using excised skins in modified FRANZ diffusion cells. The amount of zinc accumulating and penetrating the skin was determined over a 36 hour period. The accumulation of zinc was determined to be 1311 $\mu$g/g dry weight of skin, while the penetration was measured to be 3.2 $\mu$g/$cm^2$/hr.

Skin Barrier Test: Uniformity of the barrier film on the skin as shown in FIG. 5 was indicative of good barrier properties.

Anti-inflammatory: The effect of silk proteins to inhibit the hydrolysis of a model protein substrate by a fecal extract was determined. In addition, the ability of a silk protein to reduce a fecal extract-elicited pro-inflammatory response in EpiDerm™ was measured. The silk protein applied to a material was placed on the EpiDerm™ sample, both before and after application of the fecal irritant. The release of a pro-inflammatory signaling molecule Interleukin-1 alpha, was compared to that of the control not containing the silk protein.

Treatment Compositions

Treatment compositions containing water, AHCOVEL (Ahcovel Base N-62, Hodgson Chemicals, NC), SERICIN, CROSILK, and zinc sulfate monohydrate (Aldrich Chemicals, WI) were prepared according to Table 1 below. For comparison purposes, a composition was prepared containing only water and AHCOVEL.

TABLE 1

Composition Concentrations (wt. %)

| Compositions | Water | AHCOVEL | SERICIN | CROSILK 10,000 | Zinc Sulfate Monohydrate |
|---|---|---|---|---|---|
| Control | 80 | 20 | — | — | — |
| 1 | 69.1 | 20 | — | 10 | .9 |
| 2 | 69.1 | 20 | 10 | — | .9 |

Although not specifically shown in the data, silk protein emulsions, without the aid of surfactant, were applied to a substrate. Since the protein is hydrophilic, and the substrate is hydrophobic, the protein would not easily wet and saturate the substrate, and instead formed a bead on top of the substrate.

Treated Substrate

Untreated polypropylene spunbond materials (basis weight of about 0.5 ounces per square yard) were used as a substrate for the treatment compositions. The compositions of Table 1 were applied to the substrates by a low-solids batch treatment process. An 8"×12" (20.32×30.48 cm) sample of the substrate was first dipped in an acqueous treatment bath of known composition illustrated in Table 2 below.

TABLE 2

Treatment Bath Concentration as applied to the substrates

| Example | Composition (from Table 1) | Water | Ahcovel Base N-62 | Sericin | Crosilk 10,000 | Zinc Sulfate Monohydrate |
|---|---|---|---|---|---|---|
| 1 | Control | 98.8 | 1.2 | — | — | — |
| 2 | Control | 97 | 3 | — | — | — |
| 3 | Control | 94 | 6 | — | — | — |
| 4 | 1 | 98.146 | 1.2 | — | .6 | .054 |
| 5 | 1 | 97 | 1.942 | — | .971 | .087 |
| 6 | 1 | 94 | 3.883 | — | 1.942 | .175 |
| 7 | 2 | 97 | 1.942 | .971 | — | .087 |
| 8 | 2 | 94 | 3.883 | 1.942 | — | .175 |

The saturated samples were then nipped between two rubber rollers in a laboratory wringer, Type LW-1, No. LW-83A (Atlas Electric Devices, Chicago, Ill.), and subsequently dried in an oven at 60° C. for about 20 minutes or until constant weight was obtained. Nip pressure was adjusted to achieve a 100% wet pick-up (%WPU). %WPU is calculated from the following equation:

$$\%WPU = [(Ww - Wd)/Wd] \times 100,$$

where:

$Ww$ = wet weight of the nipped fabric,
$Wd$ = dry weight of the treated fabric.

Knowing the bath concentration and the %WPU, the % Add On can be calculated following equation:

$$\%AddOn = (\%BathConcentration) \times (\%WPU) \div 100$$

If, as in this example, the %WPU=100, then the % Add-On will equal the % Bath Concentration. However, other %WPU and % Bath Concentration combinations can be used to achieve similar results. Final % Add-On for each component of each example is shown Table 3 below.

TABLE 3

% Add-On for Each Example of Table 2

| Example | Ahcovel Base N-62 | Sericin | Croslik 10,000 | Zinc Sulfate Monohydrate |
|---|---|---|---|---|
| 1 | 1.2 | — | — | — |
| 2 | 3 | — | — | — |
| 3 | 6 | — | — | — |
| 4 | 1.2 | — | .6 | .054 |
| 5 | 1.942 | — | .971 | .087 |
| 6 | 3.883 | — | 1.942 | .175 |
| 7 | 1.942 | .971 | — | .087 |
| 8 | 3.883 | 1.942 | — | .175 |

The Fluid Intake Rate was determined for some of the examples of Table 3 as shown Table 4 below, according to the test as described above. As shown in the data, fluid-intake rates have not been adversely affected by addition of the treatment composition of the present invention, and the substrates, therefore, provide adequate fluid handling properties.

TABLE 4

Fluid Intake Time (sec.)

Intake Time (second)

| Example | Insult 1 | Insult 2 | Insult 3 | Insult 4 | Insult 5 |
|---------|----------|----------|----------|----------|----------|
| 2 | 2.82 | 2.83 | 3.05 | 3.21 | 3.15 |
| 3 | 2.45 | 2.43 | 2.54 | 2.47 | 2.65 |
| 5 | 2.38 | 2.41 | 2.43 | 2.35 | 2.55 |
| 6 | 2.63 | 2.69 | 2.60 | 2.72 | 2.70 |
| 7 | 2.51 | 2.72 | 2.43 | 2.32 | 2.38 |
| 8 | 2.44 | 2.56 | 2.37 | 2.38 | 2.42 |

Inhibition of the Proteolytic Activity of Fecal Extract—Silk Protein and Zinc Composition The treated substrates were tested to assess their capacity to inhibit the reaction of fecal extract with synthetic skin. The fecal extract was prepared from feces obtained from an infant on antibiotics (Sulfatrim) who had diaper rash. To prepare the extract, the feces were suspended in water and vigorously vortexed. After vortexing, the samples were held on ice prior to centrifugation at 15,000 times the force of gravity for 20 minutes. The supernatant was filtered through 0.22 micron cellulose acetate filters and stored at $-70°$ C. until use. Trypsin (molecular weight=23,500 daltons), a protease known to contribute to diaper rash, was measured in the fecal extract at a concentration of 5,850 picomoles/milliliter. Pancreatic elastase (molecular weight=25,000 daltons), a suspected contributor, was measured in the fecal extract at a concentration of 83.6 picomoles/milliliter.

The synthetic skin, EpiDerm™ 201 (MatTek Corporation, Ashland, Mass.), contained keratinocytes that release interleukin-1 alpha (IL-1 alpha) when subjected to proteases such as trypsin and pancreatic elastase. When the IL-1 alpha was released, it diffused from the skin into the liquid below the EpiDerm™. Samples of this liquid were taken and analyzed for the presence of the IL-1 alpha. Higher levels of IL-1 alpha were indicative of greater skin irritation.

To perform the experiment, 10 μL of water was applied to the surface of the synthetic skin. The treated substrates were cut into about 0.9 cm discs which were placed on top of the water on the EpiDerm™. After about a two-hour incubation at about 37° C., the discs were removed and the EpiDerm™ was insulted with 15 μL of insult liquid where each of the treated substrate discs had been. A second treated substrate disc was then placed on top of the insult liquid to simulate the diaper environment. After 11 hours at 37° C., an aliquot from the underlying liquid bathing the EpiDerm™ was removed and the amount of IL-1 alpha was quantified using the R&D Systems Interleukin-1 alpha Quantikine Kit (R&D Systems, Minneapolis, Minn.).

Four treatments were done using two samples from Table 3 and two insult liquids (fecal extract and water) as shown below in Table 5.

TABLE 5

EpiDerm ™ treatments

| Code | Example Used | Insult Liquid |
|------|--------------|---------------|
| A | 1 (Control) | Water |
| B | 1 (Control) | Fecal Extract |
| C | 4 | Water |
| D | 4 | Fecal Extract |

The results of the treatments from Table 5 are shown in Table 6 below. The application of the substrate treated with CROSILK and zinc (Code D) to the EpiDerm™ reduced the amount of interleukin-1 alpha released into the underlying media relative to the application of the materials treated with just AHCOVEL (Code B).

TABLE 6

IL-1 alpha Released (picagrams/milliliter)

| Code | Mean | Standard Deviation | Number of samples |
|------|------|--------------------|-----|
| A | 14.03 | 4.768 | 6 |
| B | 105 | 66 | 5 |
| C | 6.77 | 6.77 | 6 |
| D | 44.92 | 23.4 | 6 |

Inhibition of the Proteolytic Activity of Fecal Extract—Silk Proteins

Water soluble silk protein (SERICIN, Pentapharm AG, Basel, Switzerland) and hydrolyzed silk (CROSILK 10,000, Croda, Incorporated, Parsippany, N.J.) were individually shown to inhibit proteolytic activity in the fecal extract that has been implicated to contribute to diaper rash. Serial dilutions of the neat protein and hydrolysate were performed with 100 mM Tris-HCl pH 8.0 as the diluent. The silk protein concentrations were determined using a Macro BCA Protein Assay Reagent Kit (Pierce, Rockford, Ill.).

Fecal extract was prepared as described above for the examples of silk protein and zinc compositions. SERICIN and CROSILK (20 μL) were added to wells of a 96 white plate (Dynex, Chantilly, Va.) containing 80 μL of a 12.5 μg/ml solution of a fluorescent dye-labeled casein substrate (EnzChek Protease Assay Kit (E-6639), Molecular Probes, Eugene, Oreg.). The reaction was initiated with the addition of 100 μL of the 2 μg/ml fecal extract. Reaction of the fecal extract with the casein substrate cleaves the fluorescent dye from the substrate. Relative fluorescence units (RFUs) were collected using the Fluoroskan Ascent System (Labsystems, Incorporated, Needham Heights, Mass.) with excitation and emission filters of 485 and 538 nm, respectively. The reaction was run for 30 min. at room temperature and rates (RFU/min) from 10–20 minutes were calculated. Percent of fecal proteolytic activity remaining was determined for each concentration of SERICN and CROSILK inhibitor (Inhibited Rate/Uninhibited rate* 100).

Figure 7:
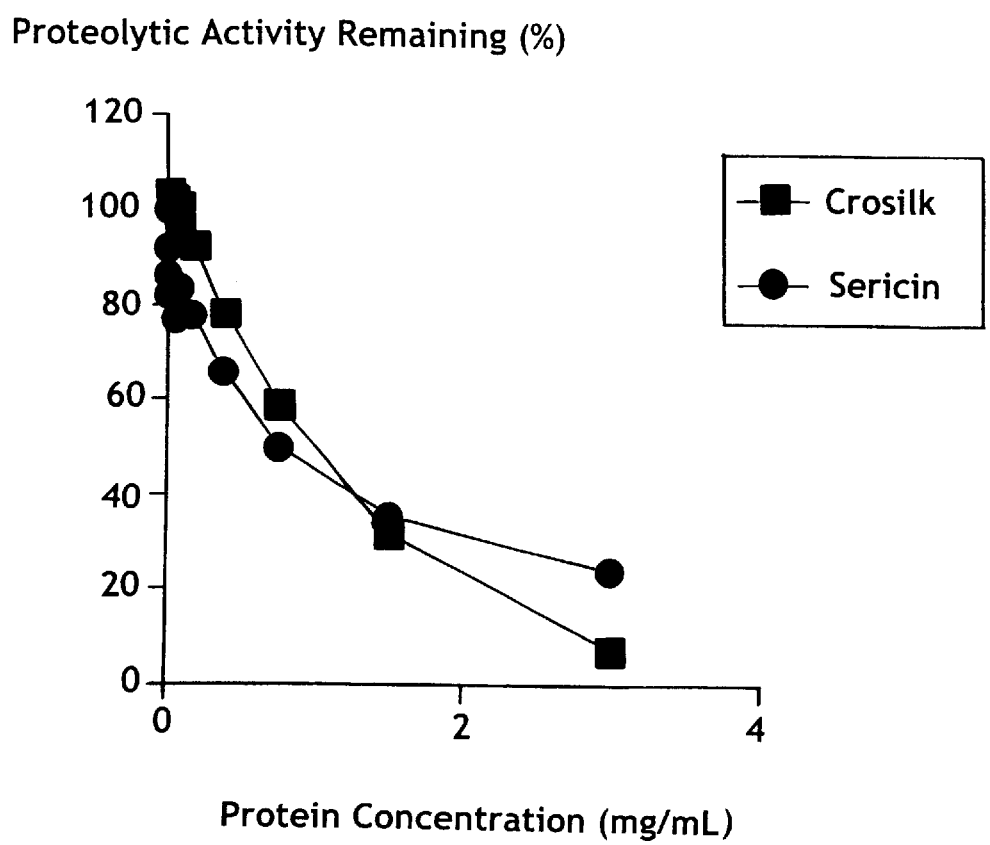
FIG. 7 is a graph comparing inhibition of proteolytic activity by silk proteins in accordance with the present invention.

A plot of the data is shown in FIG. 7, which is a graph showing reduction of proteolytic activity with increasing concentrations of both SERICIN and CROSILK. These data suggest that both molecules have the ability to neutralize proteases in feces that have been implicated to induce skin inflammation in the diaper environment (*Faecal enzymes: in vivo skin irritation,* supra).

While various patents and other reference materials have been incorporated herein by reference, to the extent there is any inconsistency between incorporated material and that of this written specification, the written specification shall control. In addition, while the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A treatment combination for imparting a liquid-mediated transfer medium to a substrate, said combination comprising a surfactant and sericin;

the surfactant including a compound selected from the group comprising ethoxylated hydrogenated fatty oils, monosaccharides, monosaccharide derivatives, polysaccharides, polysaccharide derivatives and combinations thereof;

wherein said surfactant and sericin are combined in an aqueous emulsion to form a treatment composition.

2. The treatment combination of claim 1, wherein said aqueous emulsion is a microemulsion.

3. The treatment composition of claim 1, wherein said surfactant and sericin are present at a weight ratio of about 0.01–25 wt. % sericin to about 75–99.99 wt. % surfactant.

4. The treatment composition of claim 1, wherein said emulsion further comprises 0.1 to 40 wt. % total solids.

5. The treatment composition of claim 1 further comprising an active agent.

6. The treatment composition of claim 5 wherein said active agent is a multivalent metal compound.

7. The treatment composition of claim 6 wherein said multivalent metal compound further comprises zinc salt or zinc sulfate monohydrate.

8. A substrate treated with a treatment combination, said treatment combination comprising a surfactant and a silk protein;

the surfactant including a compound selected from the group consisting of ethoxylated hydrogenated fatty oils, monosaccharides, monosaccharides derivatives, polysaccharides, polysaccharide derivatives, and combinations thereof, wherein said surfactant is a liquid-mediated transfer medium for transfer of said silk protein from said substrate to a wearer.

9. The treated substrate of claim 8 wherein said silk protein comprises sericin.

10. The treated substrate of claim 9, wherein the substrate is selected from woven fabrics, knit fabrics, nonwoven fabrics, foams, film materials and paper materials.

11. The treated substrate of claim 10, wherein the substrate comprises a nonwoven web.

12. The treated substrate of claim 11 wherein said nonwoven web is hydrophobic.

13. The treated substrate of claim 11, wherein said nonwoven web comprises a spunbond web, meltblown web, coformed web or bonded carded web.

14. The treated substrate of claim 11, wherein said substrate comprises a multilayer laminate.

15. The treated substrate of claim 9, wherein the treatment combination further comprises an active agent.

16. The treatment composition of claim 15 wherein said active agent is a multivalent metal compound.

17. The treatment composition of claim 16 wherein said multivalent metal compound further comprises zinc salt or zinc sulfate monohydrate.

18. The treated substrate of claim 8, wherein the combination is applied at a level of about 0.1–1.5% by weight surfactant relative to the basis weight of the substrate.

19. The treated substrate of claim 18, wherein the combination is applied at a level of about 0.1–1.0% by weight surfactant relative to the basis weight of the substrate.

20. The treated substrate of claim 19, wherein the combination is applied at a level of about 0.1–0.5% by weight surfactant relative to the basis weight of the substrate.

21. A personal care product comprising the treated substrate of claim 8.

22. The personal care product of claim 21, wherein the personal care product is selected from a diaper, training pant, absorbent underpant, adult incontinence product, sanitary wipe, feminine hygiene product, wound dressing and bandage.

23. The treatment composition of claim 9, wherein a fluid intake rate of said substrate is not adversely affected by addition of said treatment composition.

24. The method of transferring a thin, tenacious, substantially continuous film of silk protein to skin comprising:

a) providing a substrate;

b) applying a treatment composition to said substrate, said composition comprising a surfactant and a silk protein in combination; the surfactant including a compound selected from the group consisting of ethoxylated hydrogenated fatty oils, monosaccharides, monosaccharide derivatives, polysaccharides, polysaccharide derivatives, and combinations thereof, c) insulting said substrate with an aqueous based liquid whereby said treatment composition dissolves in said liquid, and d) transferring said treatment composition from said substrate to the skin, thereby forming a thin, tenacious, substantially continuous, film on the skin.

25. The method of claim 24 wherein said substrate is a hydrophobic nonwoven web.

26. The method of claim 25, wherein the substrate comprises a personal care product.

27. The method of claim 26 wherein said silk protein comprises sericin.

28. The method of claim 27 further comprising addition of an active agent to said substrate.

29. The method of claim 28 wherein said active agent is a multivalent metal compound comprising zinc salt or zinc sulfate monohydrate.

* * * * *